United States Patent [19]
McTighe et al.

[11] Patent Number: 5,653,765
[45] Date of Patent: Aug. 5, 1997

[54] MODULAR PROSTHESIS

[75] Inventors: Timothy McTighe, Chagrin Falls, Ohio; Jerry Kee, Palm Beach Gardens, Fla.; Bruce Shepherd, Mosman, Australia

[73] Assignee: Ortho Development Corporation, Draper, Utah

[21] Appl. No.: 368,040

[22] Filed: Jan. 3, 1995

Related U.S. Application Data

[63] Continuation of Ser. No. 269,935, Jul. 1, 1994, abandoned.
[51] Int. Cl.$^6$ ........................................... A61F 2/32
[52] U.S. Cl. ................................... 623/23; 623/18
[58] Field of Search .......................... 623/16, 18, 19, 623/20, 22, 23, 66

[56] References Cited

U.S. PATENT DOCUMENTS

| Re. 28,895 | 7/1976 | Noiles. |
| D. 339,634 | 9/1993 | Hori et al. |

(List continued on next page.)

FOREIGN PATENT DOCUMENTS

| 0050533 | 4/1982 | European Pat. Off. | 623/23 |
| 0543099 | 5/1993 | European Pat. Off. | 623/23 |
| 2580171 | 10/1986 | France | 623/23 |
| 2689001 | 10/1993 | France | 623/23 |
| 2558446 | 7/1976 | Germany | 623/23 |
| 3535158 | 4/1987 | Germany | 623/18 |
| 4320086 | 12/1994 | Germany | 623/23 |
| 2159416 | 3/1985 | United Kingdom. | |

OTHER PUBLICATIONS

Joint Implant Surgery and Research Foundation Update, *JISRF*, Apr. 1992.

Particulate Debris in Total Hip Arthroplasty: Problems and Solutions, a Scientific Exhibit at the 1993 AAOS Meeting, San Francisco, CA.

Cook et al., Journal of Biomedical Materials Research, 18, 497–512, (1984).

Yue et al., Journal of Biomedical Materials Research, 18, 1043–1058, (1984).

Zimmer "Implant Metals" product catalog Rev.2A, (Sep. 1974).

"The Freeman Total Hip Systems," Corin Medical Limited, Gloucestershire, England, 1985.

Freeman, M.A.R., "Why Resect the Neck?", The Journal of Bone and Joint Surgery, vol. 68–B, No. 3, May 1986, pp. 346–349.

Freeman, et al., in The Young Patient with Degenerative Hip Disease, Sevastik J. Goldie I (ed.), Stockholm, Sweden, 1986, pp. 281–292.

*Primary Examiner*—David Isabella
*Attorney, Agent, or Firm*—Thorpe, North & Western, L.L.P.

[57] ABSTRACT

A modular hip stem prosthesis including a separate and interchangeable stem piece and proximal shoulder piece. Coronal and sagittal slots are formed in a rounded distal end of the stem in a substantially right-angle orientation. A neck member extends angularly outward from the shoulder piece and is configured to receive a spherical hip ball for insertion into the hip socket. The proximal shoulder piece includes a cylindrical projection for insertion into an axial bore formed in an upper end of the stem. An annular lip is formed in side walls defining the axial bore, and a distal end of the cylindrical projection abuts the lip when it is inserted into the bore. Radial teeth are formed on a distal end of the cylindrical projection and mate with compatible teeth formed on the annular lip to thereby render the shoulder piece removably mountable onto the stem. A locking screw securely joins the shoulder piece with the stem. The stem piece can be unitary or made up of a separate and interchangeable distal stem piece and metaphyseal component. The shoulder piece is selectable from an array of shoulder pieces having various heights and lengths to thereby provide spacing in two dimensions between the femur and the pelvis which reduces the risk of hip dislocation without introducing the problems of leg elongation and femur splintering.

14 Claims, 3 Drawing Sheets

U.S. PATENT DOCUMENTS

| | | |
|---|---|---|
| D. 342,570 | 12/1993 | Serbousek et al. . |
| 2,719,522 | 10/1955 | Hudack . |
| 3,067,740 | 12/1962 | Haboush . |
| 3,605,123 | 9/1971 | Hahn . |
| 3,808,606 | 5/1974 | Tronzo . |
| 3,820,167 | 6/1974 | Sivash . |
| 3,840,904 | 10/1974 | Tronzo . |
| 3,848,272 | 11/1974 | Noiles . |
| 3,894,297 | 7/1975 | Mittelmeier et al. . |
| 3,943,576 | 3/1976 | Silvash . |
| 3,987,499 | 10/1976 | Scharbach et al. . |
| 4,031,571 | 6/1977 | Heimke et al. . |
| 4,051,559 | 10/1977 | Pifferi . |
| 4,068,324 | 1/1978 | Townley et al. . |
| 4,206,516 | 6/1980 | Pilliar . |
| 4,304,011 | 12/1981 | Whelan, III . |
| 4,352,212 | 10/1982 | Greene et al. . |
| 4,514,865 | 5/1985 | Harris . |
| 4,549,319 | 10/1985 | Meyer . |
| 4,670,015 | 6/1987 | Freeman . |
| 4,718,912 | 1/1988 | Crowninshield . |
| 4,790,852 | 12/1988 | Noiles . |
| 4,813,963 | 3/1989 | Hori et al. . |
| 4,822,370 | 4/1989 | Schelhas . |
| 4,846,839 | 7/1989 | Noiles . |
| 4,888,023 | 12/1989 | Averill et al. . |
| 4,908,032 | 3/1990 | Keller . |
| 5,002,578 | 3/1991 | Luman . |
| 5,116,380 | 5/1992 | Hewka et al. . |
| 5,133,772 | 7/1992 | Hack et al. . |
| 5,152,799 | 10/1992 | Lyons . |
| 5,163,963 | 11/1992 | Hewka et al. . |
| 5,171,324 | 12/1992 | Campana et al. . |
| 5,326,376 | 7/1994 | Warner et al. . |
| 5,342,366 | 8/1994 | Whitside et al. . |
| 5,360,446 | 11/1994 | Kennedy . |

MODULAR PROSTHESIS

This is a continuation of U.S. patent application Ser. No. 08/269,935 filed Jul. 1, 1994, entitled MODULAR PROSTHESIS now abandoned.

BACKGROUND OF THE INVENTION

1. Field of the Invention.

The present invention relates generally to the field of artificial joints. More particularly, it concerns a modular hip stem prosthesis with increased stability and distal flexibility to reduce thigh pain, a removably mounted, incrementally rotatable proximal shoulder with increased rotary stability, and selectable sizing of the proximal shoulder to prevent dislocation of the hip joint and to compensate for bone loss.

2. The Background Art

It is known in the art to replace the hip joint with an artificial hip stem replacement. Numerous artificial implants are available which can be installed to replace the natural hip joint with an artificial ball and socket combination. A passage called the medullary canal is reamed or bored in the upper end of the femur. A stem portion of an artificial implant is inserted into the reamed portion of the medullary canal in a secure, seated position. A neck member extends outward and away from the stem and terminates in a spherical knob for insertion into the hip in rotational contact therewith about the three major orthoganal axes.

Implants of this type have been made as a one-piece, unibody member. A hip replacement procedure using a one-piece prosthesis involves selecting a particular hip stem implant from a set of implants in order to obtain the proper size and configuration. However, the anatomy of the relevant bones is so detailed and varies so much between patients that an extensive set of prostheses is required in order to meet every conceivable anatomical condition encountered during the surgical procedure. The result is a standardized, expensive set of one-piece prostheses to cover substantially all anatomical conditions.

A partial solution to the lack of customization and affordability was attempted in the development of a series of sleeves designed to releasably receive the artificial stem. The sleeve was designed to match the contours and angles of the reamed portion of the medullary canal to provide greater rotary stability to the stem relative to the femur. Examples of sleeve and stem combinations are found in U.S. Pat. Nos. 4,790,852 and 4,846,839 (issued to Noiles on Dec. 13, 1988 and on Jul. 11, 1989, respectively). The sleeves taught therein are interchangeably mounted to the proximal end of the stem portion. The Noiles sleeve allows the surgeon to select a properly sized neck and stem piece and simply interchange the selected piece with a number of different sleeves until the proper sleeve/stem combination is found.

Although the Noiles sleeve arrangements still have restrictions, such as nonadjustability of the neck portion, the introduction of modularity into the field of hip stem prostheses has proved to be a helpful discovery. The aspect of modularity has motivated the development of hip stem prostheses having a hip stem and a mating neck assembly removably mounted on the stem. Examples of such a modular hip stem prosthesis is found in U.S. Pat. No. 5,002,578 (issued to Luman on Mar. 26, 1991). The hip stem taught in the Luman patent permits the surgeon to put together a custom hip stem prosthesis from two or more modular components. Before modularity was introduced into the art, an entire series of unibody implants was necessary for each particular component size. For example, if twenty different neck angles were desirable, each particular stem configuration would have to be reproduced twenty different times with the different neck sizes and configurations. If there were also twenty different stem configurations, these two variables alone would account for 400 different combination possibilities. Additional component variations would exponentially compound the number of unibody combinations. However, the advantages of modularity allow, in the above example, twenty different necks and twenty different stems, all of which are interchangeable with each other. Instead of 400 pieces, only forty pieces are necessary to achieve the same combinations.

The advancements made to date in the field of hip stem prostheses, while helpful, are fraught with disadvantages. Modularity alone fails to solve many of the problems which have persisted in the field. For example, the prior art hip stem devices fail to maximize the flexibility of the stem portion needed to eliminate hoop tension during insertion of the stem, and thigh pain. They also fail to provide spacing between the femur and the pelvis sufficient to prevent dislocation of the hip without introducing dangerous moment arm action of the neck capable of splintering and/or fracturing the femur. These prior art apparatus further fail to provide increased rotatory stability of the neck and precise, incremental adjustability of the neck version angle relative to the stem. Neither do the prior art devices provide a neck portion having a high degree of rotary adjustability which is removable from the stem without a significant loss of strength. The prior art also fails to adequately inhibit osteolysis caused by wear debris generation introduced by metal/metal interfacing.

OBJECTS AND SUMMARY OF THE INVENTION

It is therefore an object of the present invention to provide a modular hip stem prosthesis for replacing the hip joint.

It is an additional object of the present invention to provide such a prosthesis that is easy to install.

It is a further object of the present invention to provide such a prosthesis which inhibits wear debris generation.

It is another object of the present invention, in accordance with one aspect thereof, to provide such a prosthesis which provides increased flexibility of the stem portion.

It is a further object of the invention, in accordance with one aspect thereof, to provide such a prosthesis which provides spacing between the femur and the pelvis sufficient to prevent dislocation of the hip, without introducing dangerous moment arm action in the neck capable of splintering and/or fracturing the femur.

It is another object of the invention, in accordance with one aspect thereof, to provide such a prosthesis which provides increased rotatory stability of the neck and precise, incremental adjustability of the neck version angle relative to the stem.

It is yet another object of the invention, in accordance with one aspect thereof, to provide such a prosthesis which can compensate for bone loss in the femur.

It is still another object of the invention, in accordance with one aspect thereof, to provide such a prosthesis which provides a neck portion having a high degree of rotary adjustability which is removable from the stem without a significant loss of strength.

The above objects and others not specifically recited are realized in an illustrative embodiment of a modular hip stem prosthesis. Coronal and sagittal slots are formed in a rounded distal end of the stem in a substantially right-angle orientation with each other. A neck member is attached to a proximal shoulder piece and is configured to receive a spherical hip ball for insertion into the hip socket. The proximal shoulder piece includes a cylindrical projection for insertion into an axial bore formed in the upper end of the stem. An annular lip is formed in side walls defining the axial bore, and a distal end of the cylindrical projection abuts the lip when it is inserted into the bore. Radial teeth are formed on a distal end of the cylindrical projection and mate with compatible teeth formed on the annular lip to thereby render the shoulder piece removably mountable onto the stem. A locking screw securely joins the shoulder piece with the stem. The shoulder piece is selectable from an array of shoulder pieces having various thicknesses and widths to thereby provide spacing in two dimensions between the femur and the pelvis which reduces the risk of hip dislocation without introducing the problems of leg elongation and femur splintering. The shoulder piece size can also be selected for the purpose of compensating for bone loss in the femur.

Additional objects and advantages of the invention will be set forth in the description which follows, and in part will be apparent from the description, or may be learned by the practice of the invention. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the subsequent detailed description presented in connection with the accompanying drawings in which.

DETAILED DESCRIPTION OF PRESENTLY PREFERRED EMBODIMENTS

Reference will now be made to the drawings wherein like structures will be provided with like reference numerals.

FIGS. 1-4 illustrate the main features of a modular hip stem prosthesis, generally designated at 10. The prosthesis 10 includes an elongate stem member 12, a proximal shoulder 14, and a locking screw 16 for fastening the proximal shoulder 14 to the stem member 12.

The stem member 12 includes an elongate, cylindrical shaft 18 having a collar 20 at a proximal end thereof, and a plurality of longitudinal flutes 22 at a distal end thereof. The stem member 12 further includes a rounded, distal tip 24 and coronal and sagittal slots 25 and 27, respectively, formed in said distal tip 24. An axial bore 26 is formed in a proximal end 20a of the collar 20, said bore 26 being defined by substantially cylindrical side walls 28. The axial bore 26 includes a narrow bore portion 26a and a wide bore portion 26b, such that an annular lip 30 is formed in the side walls 28 at a boundary between said narrow and wide bore portions. First serrated contacting structure 32 is formed on the annular lip 30. Female threads 23 are formed in the side walls 28 of the narrow bore portion 26a.

The collar 20 is configured with a generally ellipsoidal shape, and a series of generally elliptical terraces 34 define the contour of an outer surface of the collar 20. The collar 20 is generally widest at the proximal end 20a and gradually tapers inwardly from said proximal end 20a to the distal end of the stem 12 to meet with the shaft 18 at a distal collar end 20b.

The proximal shoulder 14 includes an angularly offset neck 40 which terminates in a tapered section 42. The tapered section 42 operates as a mounting piece for a hip ball 70. The dimensions of the proximal shoulder 14 include a thickness dimension 44 and a width dimension 46. A cylindrical projection 48 is disposed on a lower surface 50 of the shoulder 14 and dimensionally corresponds with the wide bore portion 26b of the axial bore 28 for telescopic insertion thereinto. Second serrated contacting structure 52 is formed on a distal end of the cylindrical projection 48 and dimensionally corresponds with the first serrated contacting structure 32 and is engageable therewith. The shoulder 14 includes a throughbore 54 formed therein and a countersink 56 for receiving the locking screw 16. The locking screw 16 includes male threads 60 which dimensionally correspond with the female threads 27 and are engageable therewith.

Figure 1:
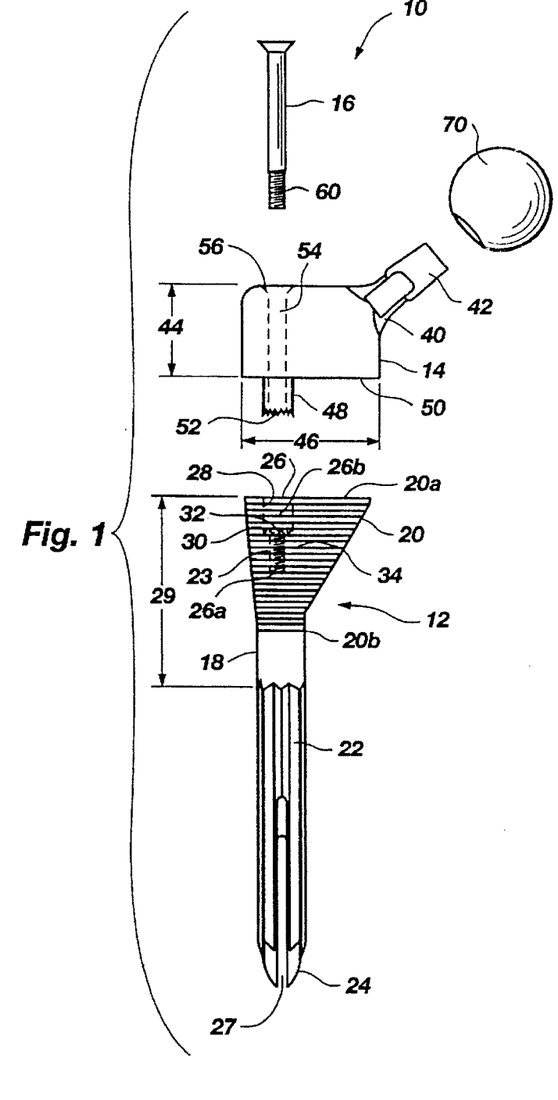
FIG. 1 illustrates an exploded, side view of a modular hip stem prosthesis made in accordance with the principles of the present invention.
Figure 2:
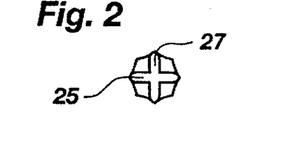
FIG. 2 illustrates a front view of the tip of the stem portion of the modular hip stem prosthesis of FIG. 1.
Figure 3:
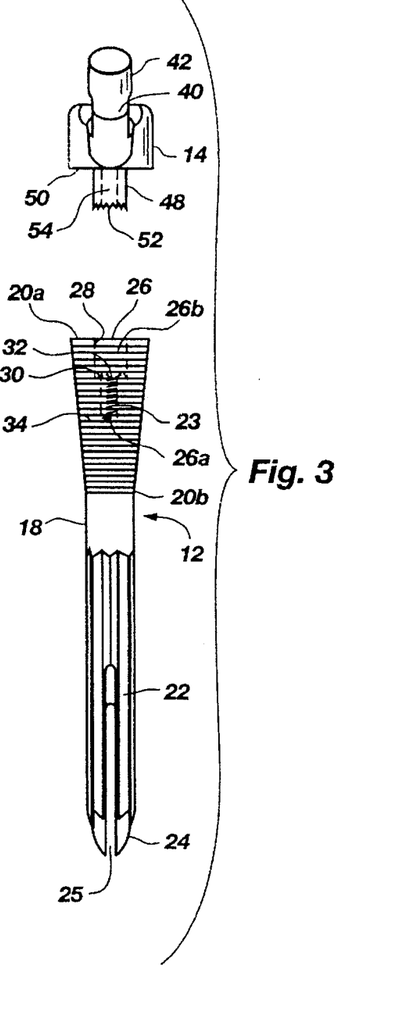
FIG. 3 illustrates an exploded, front view of the modular hip stem prosthesis of FIG. 1.
Figure 4:
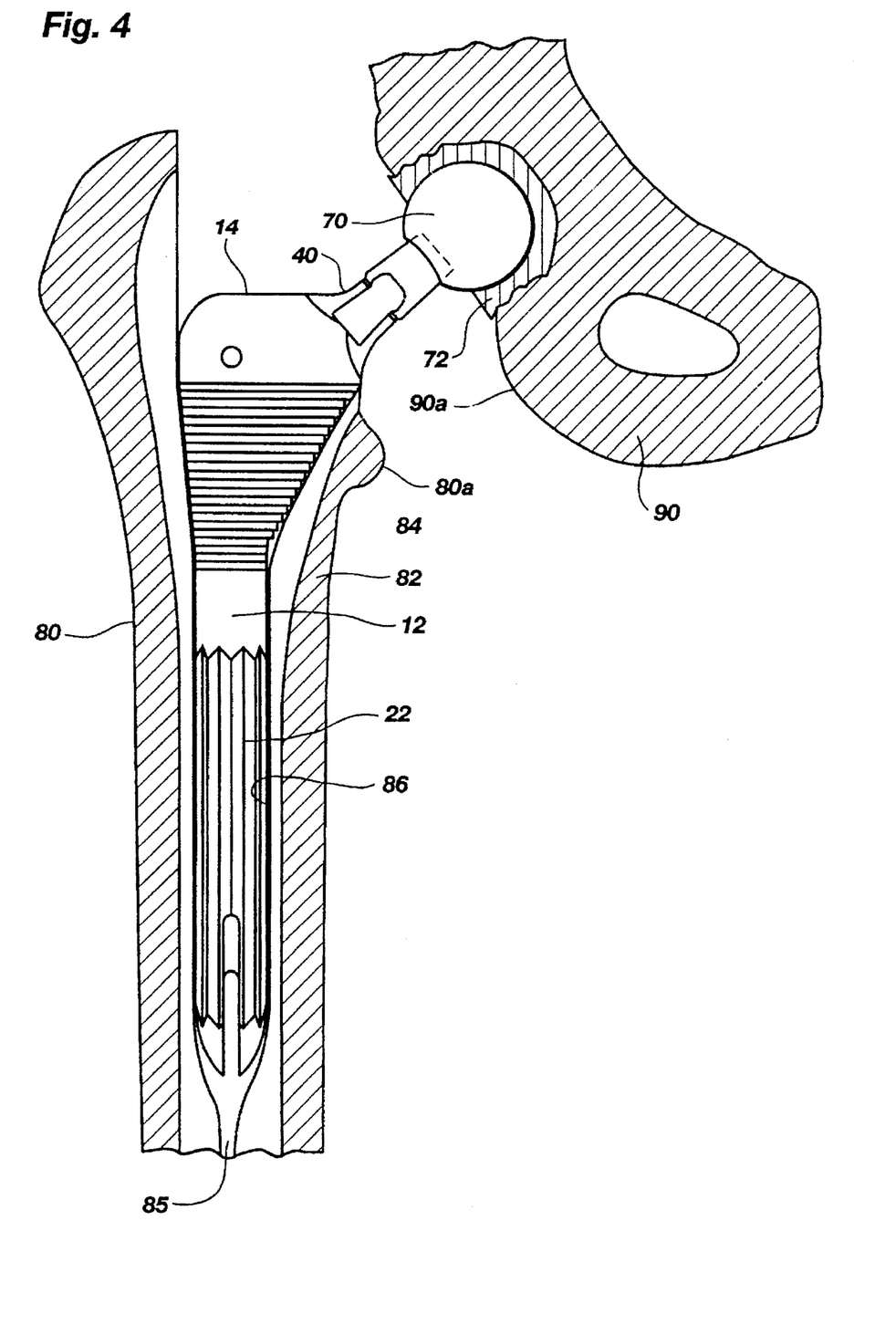
FIG. 4 illustrates an assembled, side view of the modular hip stem prosthesis of FIGS. 1-3 implanted within a femur and pelvis.

The general objectives of hip stem prostheses will now be discussed for a fuller understanding and appreciation of applicants' discovery. Referring now to FIG. 4, it is shown that the stem member 12 is implanted in the patient's femur 80 which has an outer shell 82 of hard bone surrounding an inner core 84 of soft bone or medulla defining a medullary canal 85. The motion of the hip joint occurs about the spherical hip ball 70. When replacing the hip joint with an artificial hip stem prosthesis, the surgeon removes a certain amount of the inner core 84 in the upper end of the femur 80 to form a channel 86 within the medullary canal 85, by simple straight reaming. The surgeon's preparation of the channel 86 is dictated to a large extent by the characteristics and shape of the upper end of the femur 80. The channel 86 in turn dictates the size of the stem member 12 to be selected by the surgeon.

A next step is to match the contour of the upper portion of the channel 86 to the exterior contour of the collar 20. The surgeon makes special efforts to obtain the best fit possible between the stem member 12 and the femur 80 in order to provide the best possible stress transfer distribution between the prosthesis 10 and the femur 80. It will be appreciated that the terraces 34 are forced into engagement with the surrounding intra medullary bone 84 to block rotational movement of the stem 12, and to stimulate supporting bone growth therearound. The flutes 22 also operate to provide rotary stability to the stem member 12 relative to the femur 80. Insertion of the stem 12 into a properly prepared femur 80 also causes slight compression of the coronal slot 25 shown in FIGS. 2 and 3. This compressive action causes the longitudinal flutes 22 to be resiliently urged into contact with the surrounding bone 84. The stem 12 is thereby securely engaged within the femur 80.

After the stem member 12 has been properly implanted into the femur 80, the proximal shoulder 14 is selected from a shoulder set and joined to the collar 20 of the stem member 12. The hip ball 70 is attached to the tapered section 42 of the neck 40 either before or after the proximal shoulder 14 is joined to the collar 20. The hip ball 70 is implanted into the pelvis 90 to substantially complete the hip joint replacement procedure. Dome structure 72 and/or similar structure can be inserted into the pelvis 90 as known in the art to accommodate the hip ball 70. Additional details of the method and procedures known in the art for preparing the femur 80 and pelvis 90 for artificial hip joint replacement can learned from the patents referred to above in the BACKGROUND OF THE INVENTION section. It is to be understood that the principles of the invention can be applied to any articulation and are thus not limited to applications involving the hip joint.

The purpose and interrelationship of the elements, features and concepts identified above will be discussed in more detail below.

One of the many challenges facing the surgeon in a hip replacement procedure is inhibiting what is referred to in the field as thigh pain. The everyday, repetitive movements and bending of the leg introduces stress in the femur 80, a substantial portion of which is transmitted through the inner core 84 of soft bone which has a degree of flexibility. It will be appreciated that if the stem 12 is less flexible than the portion of the inner core 84 which it replaces, less stress will be distributed through the normal stress paths of the femur. Instead, the stress finds alternative, abnormal distribution paths though the thigh, thereby causing thigh pain.

The challenge in reducing thigh pain is heightened by the fact that the stem 12 must have enough strength to withstand the normal bending and tension forces introduced thereto by the hip joint. Although materials have been developed in an attempt to accommodate all of these forces and stress transfers, the problem of thigh pain has remained. The coronal slot 25 was introduced to impart a limited degree of lateral flexibility to the stem 12. As force is applied to the femur 80, the coronal slot 25 allows the stem 12 to compress somewhat to decrease some of the alternative stress distribution, thereby reducing thigh pain somewhat.

Another challenge facing the surgeon is inhibiting what is referred to in the field as hoop stresses. It is preferred to form the channel 86 to be somewhat narrower than the stem member 12 in order to provide a tight fit between the flutes 22 and the surrounding bone 84. This induces the flutes 22 to be urged into a greater degree of contact with the bone 84 during and after insertion of the stem 12 into the channel 86, thereby providing greater rotary stability between the stem 12 and the femur 80. However, this approach increases the chances of hoop stress and resulting intra-operative femoral fractures during insertion of the stem 12 into the channel 86.

Applicants have discovered that coronal slot 25 is only partially successful in reducing thigh pain because it only permits flexibility of the stem 12 in one direction. However, one of the risks involved in forming additional slots in the distal tip 24 of the stem member 12 is decreased bending stiffness and strength of said stem member. This appeared to cause a "catch-22" situation: Optimal strength and bending stiffness in the stem member 12 (i.e. one slot or no slots) versus optimal flexibility of said stem member 12 (many slots) is necessary to reduce thigh pain.

Applicants have discovered that introduction of the sagittal slot 27 effectively reduces both hoop stress and thigh pain by introducing flexibility in the stem member 12 in a second direction which is oriented at substantially a right angle relative to the direction of flexibility of the coronal slot 25. It will be appreciated that the combination of the second, or sagittal slot 27 with the coronal slot 25 effectively provides flexibility in all radial directions normal to the stem 12. Thus, while the coronal slot 25 provides flexibility in only one plane, its combination with sagittal slot 27 provides flexibility in an infinite number of planes. This effectively provides flexibility in torsion to the stem 12. Further, if the sagittal slot 27 is formed to be shorter than the coronal slot 25, sufficient strength and bending stiffness in the stem member 12 is preserved. This discovery can be used in any prosthetic component. Although it is preferred that the slots 25 and 27 be oriented at substantially a right angle, the angular orientation between them may vary. Many different length combinations can be used for the coronal and sagittal slots 25 and 27, and it is presently preferred that the sagittal slot 27 have an average length which is approximately sixty percent of an average length of the coronal slot 25. It is also preferred that the slots 25 and 27 be defined by substantially planer side walls and in substantially parallel orientation with the stem member 12. It is to be understood that different lengths and diameter of the stem member 12 can be made. Further, the stem member 12 can be made in various bowed configurations as well as the straight configuration shown, in order to accommodate the various anatomical conditions.

Another challenge faced by the surgeon is inhibiting hip dislocation. It is important that there be sufficient spacing between the lesser trochanter 80a and the inferior aspect of the pelvic rim 90a. Otherwise, certain movements may cause said lesser trochanter 80a to impinge upon said pelvic rim 90a to thereby pop the pelvis 90 off of the ball 70 and dislocate the hip. This spacing is a function of the angular orientation of the neck 40, as well as the length of the neck 40. However, applicant has discovered that varying the length and angular orientation of the neck 40 as a solution to the problem of dislocation consequently introduces other problems. For example, the patient's leg may become elongated by an increase in the length of the neck 40, since said neck 40 is angled relative to the femur 80. Further, increasing the length of the neck 40 necessarily increases the moment arm action of said neck 40. The natural hip design and femur strength can only accommodate a certain level of moment action applied to an artificial stem 12 implanted inside the femur. A longer neck 40 with its increased moment arm increases the risk of splintering and fracture of the femur 80. Therefore, prior to applicants' discovery, some anatomical situations have required the surgeon to strike a balance between the risks of hip dislocation and femur fracture. Reducing the risk of hip dislocation increased the risk of femur fracture and leg elongation, and vice versa.

Applicants have discovered that orientation and spacing in vertical and horizontal dimensions operate to reduce the risk of hip dislocation without posing additional risk of femur fracture and leg elongation. By increasing the dimensions of the thickness 44 and/or the width 46 of the proximal shoulder 14, the pelvis 90 is pushed away from the femur 80 without elongating the leg or unduly increasing the moment arm action of the neck 40. The surgeon can combine variation of the dimensions 44 and/or 46 with variation in anteversion or retroversion of the neck/pelvis orientation relative to the femur 80 to achieve optimal spacing between the lesser trochanter 80a and the pelvic rim 90a. Variation of the thickness 44 also operates to provide structural support to compensate for bone loss in the femur 80.

The dimensions 44 and 46 of the proximal shoulder 14 can be varied in a number of ways. A preferred way is to provide a series of proximal shoulder pieces 14 for selection by the physician, each having different dimensions 44 and/or 46. It is important to note that most of the load imposed upon the femur 80 is cooperatively absorbed by, and transferred through, the proximal shoulder 14 and a proximal portion 29 of the stem 12. Increasing the dimensions 44 and 46, instead of the length of the neck 40, operates to strengthen these critical load absorbing elements and maintain a proper stress transfer therethrough, instead of developing undue moment action in the neck 40. It is currently preferred to vary the thickness 44 of the proximal shoulder 14 in increments of ten millimeters, and to vary the width 46 in increments of four millimeters, although other incremental variations are within the scope of the invention.

Other challenges facing the surgeon in a hip joint replacement procedure include achieving rotary stability and proper angular orientation between the proximal shoulder 14 and the stem 12. Prior art attempts to meet these challenges include forming a tapered fit between a tapered shaft portion extending from the neck into a correspondingly tapered bore in the stem. The taper is usually configured with approximately a three degree taper, referred to in the art as a Morse taper, and is impressively strong in torsion. However, this solution also introduces other problems. It is difficult, if not impossible, for the surgeon to vary the angle between the neck 40 and the stem 12 with precision and accuracy. For example, a surgeon attempting to rotate the neck by ten degrees could only do so by estimating.

A further problem in tapered engagements is the fact that breaking the tapered engagement and then re-engaging the tapered members results in a significant loss of torsional strength. For example, if a surgeon must break the tapered fit in order to re-position the neck 40, the strength of the subsequent fit is much less. One study measured the decrease in torsional strength between a tapered sleeve/stem interface subject to disengagement and reimpaction to be between 16.7 percent and 35.7 percent. See Stephen D. Cook, Ph. D., "Torsional Resistance And Wear Of A Modular Sleeve/Stem Hip System," Joint Implant Surgery and Research Foundation Update News, April, 1992. The Cook study's conclusion on the torsional strength capability offered by such tapered engagements, especially those involved in hip stem prostheses, is that "[t]he recommended feature of readjusting stem anteversion by repeated disengagement and impaction of the sleeve/stem interface should be discouraged because of the significant reduction in torsional resistance." Id. Thus, the relevant literature actually teaches away from stem adjustments in modular hip stem prostheses even though adjustability is a main purpose of modular prostheses.

Still another problem with tapered engagements is the fact the surface area of significant contact between tapered surfaces has been found to occur primarily at the proximal and distal regions of contact. See Cook, "Torsional Resistance And Wear Of A Modular Sleeve/Stem Hip System," cited above. It has been found that the problem of non-uniform tapered engagement may be the result of distortion caused by high temperature sintering processes. Id. The process of sintering is used to apply porous coating to the exterior surface of the elliptical terraces 34 to further enhance bone ingrowth.

An additional problem in the art of tapered engagements is that the non-tapered structure of the two components to be joined must not be in contact. Otherwise, the integrity of the tapered fit would likely be compromised, because any non-tapered contact between the adjoining components could disturb the tapered fit. For example, if the projection 48 of FIGS. 1–2 were designed with a taper to mate with a tapered bore (which it is not), opposing surfaces 50 and 20a should not be touching. However, all modular metal/metal contact points generate wear debris. When wear debris is released into the body, it causes osteolysis. The necessary spacing required in the prior art to preserve a tapered fit increases the chances for wear debris to be released out of the prosthesis and into the natural areas of the joint to cause the osteolysis.

The additional problems introduced by the Morse taper approach are overcome by the cylindrical projection 48 and wide bore portion 26a, and the engagement between the first and second serrated contacting structures 32 and 52. It will be appreciated that the toothed configuration of the structures 32 and 52 permit the surgeon to vary the angular orientation of the neck 40 by a precise, measurable amount. Further, the combination of the engaging structures 32 and 52 and the locking screw 16 provides rotary stability far superior to that accomplished by the Morse taper approach. It is preferred that serrated contacting structures 32 and 52 each include 36 teeth of substantially common dimension, such that rotation of the shoulder 14 by one tooth is equivalent to a ten degree rotation. It is also preferred that the point of each tooth be defined by an angle of approximately sixty degrees for optimal rotary strength. Rotational forces applied to the neck 40 and/or shoulder 14 are thus counteracted by the engagement between the serrated contacting structures 32 and 52. Forming the structure 52 on the distal end of the cylindrical projection 48 provides further stability to the proximal shoulder 14, since the projection 48 radially abuts against the side walls 28 for added strength. This is thus superior to forming the structure instead on the lower surface 50 of the shoulder 14, since no additional radial abutment occurs.

It will be appreciated that the toothed engagement between structures 32 and 52 can be taken apart and re-engaged without the significant loss of torsional strength experienced in the prior art, since there is no tapered engagement to be violated. It will also be appreciated that the high temperatures produced by sintering processes do not operate to weaken the torsional strength achieved by the engaging structures 32 and 52, again because there is no tapered engagement to be violated.

It will further be appreciated that the unique design which eliminates the need for a tapered engagement thereby allows the surfaces 50 and 20a to contact. This provides the significant advantage that any wear debris generated at the metal/metal contact points will remain trapped within the prosthesis. An embodiment can be developed to allow for a maximum sealing contact pressure between the surfaces 50 and 20a to thereby prevent wear debris from being released between said surfaces.

It is to be understood that a principle aspect of the invention is the adjustability of the version angle of the neck 40, in combination with variation of the dimensions 44 and 46 of the proximal shoulder 14. It is essential that the ball 70 and its orientation relative to the proximal shoulder 14 and stem 12 match the normal position of the femoral head to enable correct mechanical balance between abductor forces as known in the art. The measured, incremental variability of the position of the neck 40 and the variability of the dimensions 44 and 46 operate to provide any desirable combination in the vertical height, version angle, and medial offset of the prosthesis. The correct position of the ball 70 relative to the proximal shoulder 14 and stem 12 can thereby be achieved to avoid nerve palsy, avoid reduced range of motion, hip dislocations, shortening of the abductor moments, and torsional forces placed on the femoral implant.

It is further to be understood that the cylindrical projection 48 may instead be formed on the surface 20a of the collar 20, and the axial bore 26 and the mating structure formed therein may instead be formed in the lower surface 50 of the proximal shoulder 14.

Figure 5:
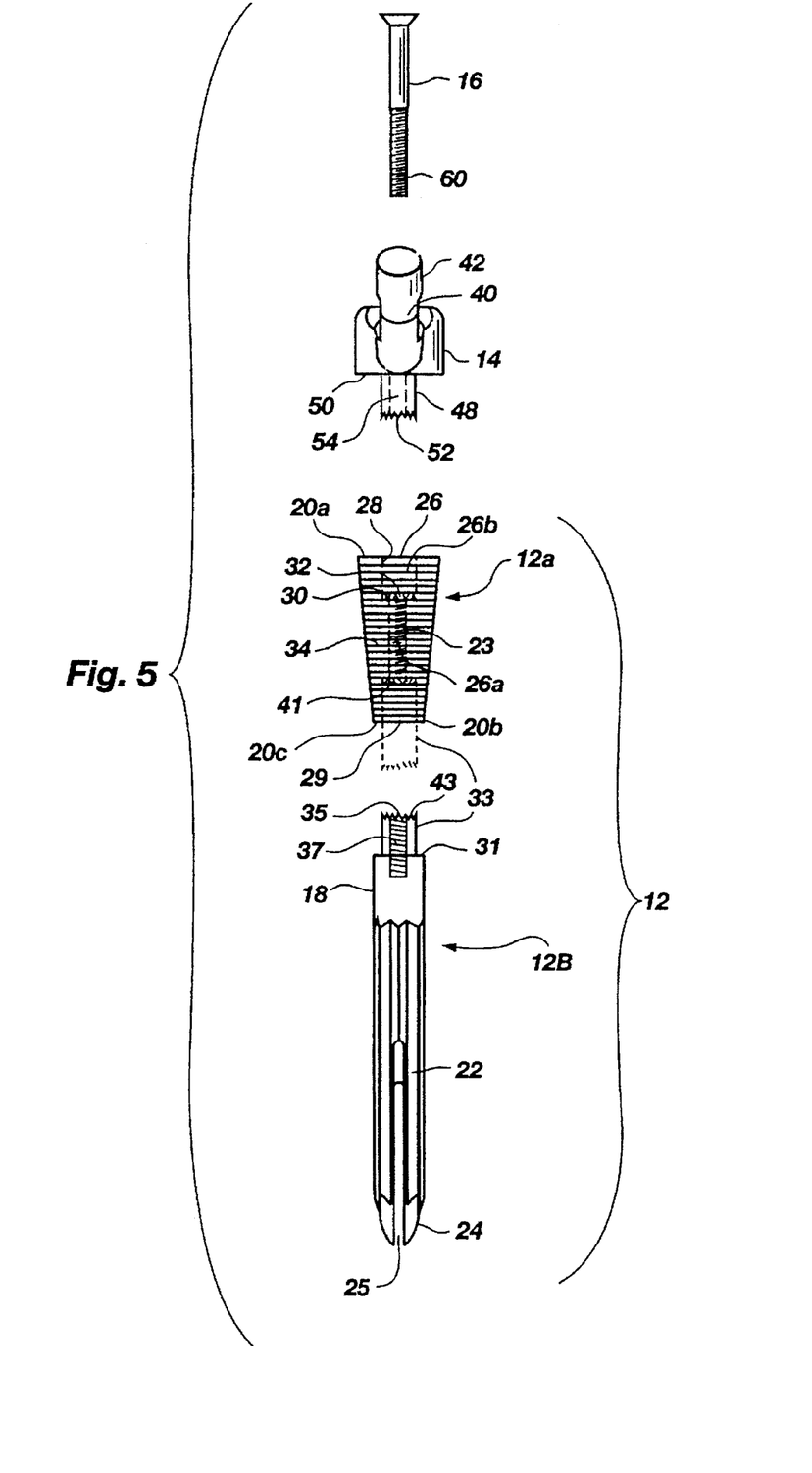
FIG. 5 illustrates an exploded, front view of an alternative embodiment of the modular hip stem prosthesis of FIG. 1.

An alternative embodiment of the present invention is illustrated in FIG. 5. The stem member 12 is separated into a second shoulder piece 12a and a distal stem piece 12b. The distal stem piece 12b is interchangeably lockable with the second shoulder piece 12a with substantially the same structures and combinations involved in interchangeably locking the proximal shoulder 14 onto the stem member 12. Accordingly, the second shoulder piece 12a includes a second axial bore 29 in substantially co-axial orientation with the axial bore 26, and in communication with the narrow bore portion 26a. A second projection 33 is formed on a proximal end 31 of the distal stem 12b, and extends outward therefrom for telescopic insertion into the second axial bore 29. The second projection 33 includes a third axial bore 35 formed therein which is defined by side walls having second female threads 37 formed therein. When the second projection 33 is inserted into the second axial bore 29, the second female threads 37 meet the female threads 23. The locking screw 16 is thereby permitted to mate with the threads 23 and 37 simultaneously to securely join together the proximal shoulder means 14, the second shoulder piece 12a, and the distal stem 12b.

It will be appreciated that the embodiment of FIG. 5 introduces further modularity into the prosthesis 10. Serrated contacting teeth 41 and 43 are dimensionally configured to mating engage in the same manner as serrated contacting structure 32 and 52. Therefore, not only is the proximal shoulder 14 incrementally rotatable tooth-by-tooth relative to the second shoulder piece 12a, but said second shoulder piece 12a is in turn incrementally rotatable tooth-by-tooth relative to the distal stem piece 12b. It is preferable that the teeth structures 32, 52, 41, and 43 have substantially common dimensional configurations. The advantages offered by the embodiment of FIG. 5 include increased rotatably fitting and customization with rotatable stability between the second shoulder piece 12a and distal stem 12b of a higher strength than that achievable with the prior art Morse tapered fit.

Referring still to FIG. 5, it is to be understood that the second projection 33 may instead be disposed on a lower surface 20c of the second shoulder piece 12a as shown in phantom line. The second projection 33 would extend outward from the second shoulder piece 12a in much the same way that the cylindrical projection 48 extends outward from the lower surface 50 of the shoulder 14. The second axial bore 29 would be formed in the proximal end 31 of the distal stem 12b. This configuration may require the screw 16 to be longer.

It is further to be understood that the proximal shoulder 14 and the second shoulder piece 12a could be formed to be a one-piece member called a proximal body. In this configuration, the proximal body would be modular relative to the distal stem piece 12b, and the modularity between the proximal shoulder 14 and the second shoulder piece 12a would of course be eliminated. The advantages and related aspects discussed above generally relative to applicants' unique tooth-to-tooth contacting structures apply equally to this alternative embodiment. Therefore, the phrase "proximal shoulder" as used herein refers to the component 14 of FIGS. 1, 3 and 5, and the phrase "proximal body" as used herein refers to a one-piece member comprising both the proximal shoulder 14 and the second shoulder piece 12a.

The present invention represents a significant advance in the field of hip stem prostheses. The novel elements set forth by applicant herein, including the sagittal slot 27, the engaging serrated contacting structures 32 and 52, and the variability of the dimensions 44 and 46, operate to provide the important advantages discussed herein without introducing the disadvantages of the prior art devices. The unique method of customizing the prosthesis 10 to specific anatomical conditions enhances the utility thereof. It will be appreciated that the principles of the invention may be used in prostheses for other joints, such as the knee and shoulder joints. The problems noted above and others not discussed are overcome to a significant degree by the present invention. Those skilled in the art will appreciate from the preceding disclosure that the objectives stated above are advantageously achieved by the present invention.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A modular prosthesis implantable into an end of a first bone in a patient for transferring mechanical stress between said first bone and a second bone member, said prosthesis comprising:

stem means for inserting into a passage formed in an end of the first bone, said stem means having an axial bore formed in a proximal end thereof which is defined by side walls and a bottom contacting face, said stem means further including:
(i) means for providing rotary stability to said stem means relative to the first bone to thereby inhibit rotational movement of said stem means within the passage; and
(ii) first serrated contacting structure formed in the bottom, contacting face as an integral part thereof;

proximal shoulder means having first and second ends and further including:
(i) neck means disposed on the second end of said shoulder means for connection with the second bone member; and
(ii) a mating projection disposed on the first end of the shoulder means and extending outward therefrom to a distal contacting face, said projection being dimensionally configured for telescopic insertion into the axial bore in an abutting relationship between the side walls thereof and including second serrated contacting structure formed on the distal contacting face and being dimensionally configured for engagement with the first serrated contacting structure to thereby restrain rotation of the shoulder means relative to the stem means.

2. A prosthesis as defined in claim 1 wherein the first and second serrated contacting structures comprise a first and second set of teeth, respectively, such that the proximal shoulder means is incrementally rotatable tooth-by-tooth relative to the stem means.

3. A prosthesis as defined in claim 2 wherein the first and second set of teeth each comprise thirty-six teeth of substantially common dimensions, such that incremental rotation of the proximal shoulder means relative to the stem means is equivalent to approximately ten degrees per tooth.

4. A prosthesis as defined in claim 2 wherein each tooth terminates in a point which defines an angle within a range of approximately fifty degrees to seventy degrees.

5. A prosthesis as defined in claim 1 wherein the side walls defining the axial bore are substantially cylindrical, and wherein the mating projection is substantially cylindrical.

6. A prosthesis as defined in claim 1 wherein at least a portion of the side walls defining the axial bore include first female threads formed thereon, and wherein the proximal shoulder means includes a throughbore formed therein which extends through the cylindrical, mating projection, said prosthesis further comprising a locking screw for insertion into the throughbore and including male threads configured for engagement with said female threads to thereby securely join the proximal shoulder means with the stem means.

7. A prosthesis as defined in claim 6 wherein the stem means further comprises a second shoulder component and a distal stem releasable connectable with said second shoulder component such that the axial bore and bottom contacting face respectively constitute a first axial bore and first contacting face formed in a first end of said second shoulder, said second shoulder further including a second axial bore formed in an opposing second end thereof which is defined by side walls and a second contacting face, and third serrated contacting structure formed in the second contacting face, such that the portion of the first axial bore having female threads communicates with the second axial bore, wherein a proximal end of the distal stem includes a second mating projection formed thereon and extending outward therefrom to a distal contacting face and being dimensionally configured for telescopic insertion into the second axial bore in an abutting relationship with the side walls defining said second axial bore, said second mating projection further including fourth serrated contacting structure formed in the distal contacting face thereof which is dimensionally configured for engagement with the third serrated contacting structure, said second mating protection also including a third axial bore formed therein being defined by side walls having second female threads formed therein such that when the mating projection of the distal stem is inserted into the second axial bore, the second female threads meet the first female threads to thereby permit the locking screw to mate with the first and second female threads simultaneously to thereby securely join together the proximal shoulder means, the second shoulder, and the distal stem.

8. A prosthesis as defined in claim 7 wherein the first, second, third and fourth sets of serrated contacting structure comprise first, second, third and fourth sets of radial pointed teeth, said first and second sets of teeth being of substantially common dimension and said third and fourth sets of teeth being of substantially common dimension, such that the proximal shoulder means is incrementally rotatable tooth-by-tooth relative to the second shoulder piece, which is in turn incrementally rotatable tooth-by-tooth relative to the distal stem, each incremental rotational movement being equivalent to a predetermined number of degrees per tooth.

9. A prosthesis as defined in claim 6 wherein the stem means further comprises a second shoulder component and a distal stem releasably connectable with said second shoulder component such that the axial bore and bottom contacting face respectively constitute a first axial bore and first contacting face formed in a first end of said second shoulder, said distal stem further including a second axial bore formed in a proximal end thereof which is defined by side walls, and a second contacting face, and third serrated contacting structure form in the second contacting face, said second shoulder further including a second mating projection formed on a distal end thereof and extending outward therefrom to a distal contacting face and being dimensionally configured for telescopic insertion into the second axial bore in an abutting relationship with the side walls defining said second axial bore, said second mating projection further including fourth serrated contacting structure formed in the distal contacting face thereof which is dimensionally configured for engagement with the third serrated contacting structure of said second axial bore, said first axial bore formed in the second shoulder being a throughbore extending through the second axial projection such that the first female threads extend between the first contacting face in the second shoulder piece and a distal end of said second axial projection, wherein a portion of the second axial bore resides below the second contacting face and includes second female threads formed thereon such that when the second mating projection on the second shoulder piece is inserted into the second axial bore, the second female threads meet the first female threads to thereby permit the locking screw to mate with the first and second female threads simultaneously to thereby securely join together the proximal shoulder means, the second shoulder, and the distal stem.

10. A prosthesis as defined in claim 1 wherein the second bone member comprises a hip, and wherein the neck means is configured for receiving a joint motion surface in a secure, fixed position thereon for insertion into a joint of the hip to thereby cause the neck means to be connected to the hip.

11. A prosthesis assembly comprising the prosthesis as defined in claim 1 and further including an array of shoulder pieces which vary in size in an axial dimension relative to the stem means.

12. A prosthesis assembly comprising the prosthesis as defined in claim 1 and further including an array of shoulder pieces which vary in size in a lateral dimension relative to the stem means.

13. A prosthesis as defined in claim 1, wherein the stem means includes a coronal slot formed in the distal end thereof to thereby provide a limited degree of lateral flexibility to the stem means in a first direction, and a sagittal slot formed in said distal end in a substantially right-angle orientation with said coronal slot to thereby provide a limited degree of lateral flexibility to the stem means in a second direction which is oriented at substantially a right angle relative to the first direction.

14. A modular prosthesis implantable into an end of a first bone in a patient for transferring mechanical stress between said first bone and an adjacent articulation, said prosthesis comprising:

stem means for inserting into a passage formed in an end of the first bone, said stem means having an axial bore formed in a proximal end thereof which is defined bu side walls and a bottom contacting face, said stem means further including:
  (i) means for providing rotary stability to said stem means relative to the first bone to thereby inhibit rotational movement of said stem means within the passage; and
  (ii) first serrated contacting structure formed in the bottom, contacting face as an integral part thereof;
a proximal body having first and second ends and further including:
  (i) means disposed on the second end of said proximal body for connection with the articulation; and
  (ii) a mating projection disposed on the first end of the proximal body and extending outward therefrom to a distal contacting face, said projection being dimensionally configured for telescopic insertion into the axial bore in an abutting relationship between the side walls thereof and including second serrated contacting structure formed on the distal contacting face and being dimensionally configured for engagement with the first serrated contacting structure to thereby restrain rotation of the proximal body relative to the stem means.

* * * * *